United States Patent [19]

Wang

[11] 4,137,310

[45] Jan. 30, 1979

[54] METHOD FOR THE CONTROL OF CATTLE GRUBS EMPLOYING A PHENYLENE BIS[IMINO(THIO]CARBONYL)DIPHOSPHOR(THIO)-AMIDIC ACID ESTER

[75] Inventor: Guang T. Wang, Princeton Junction, N.J.

[73] Assignee: American Cyanamid Company, Stamford, Conn.

[21] Appl. No.: 912,812

[22] Filed: Jun. 5, 1978

[51] Int. Cl.² .............................................. A61K 31/66
[52] U.S. Cl. ................................................... 424/204
[58] Field of Search ......................................... 424/204

[56] References Cited

U.S. PATENT DOCUMENTS 4,086,336   4/1978   Owen et al. .................... 424/204

Primary Examiner—Sam Rosen
Attorney, Agent, or Firm—Harry H. Kline

[57] ABSTRACT

There is provided a method for controlling the larvae of heel flies which parasitize ruminants and other warm-blooded animals by administering to said animals an effective amount of an unsubstituted or substituted phenylene bis[imino(thio)carbonyl]diphosphor(thio)amidic acid ester.

10 Claims, No Drawings

METHOD FOR THE CONTROL OF CATTLE GRUBS EMPLOYING A PHENYLENE BIS[IMINO(THIO]CARBONYL)DIPHOSPHOR(-THIO)-AMIDIC ACID ESTER

The present invention relates to a method for the control of the larvae of flies of the family Hypodermatidae, also referred-to as cattle grubs or ox warbles, which parasitize ruminants such as cattle, goats and sheep, and occasionally other warm-blooded animals and humans. More particularly, it relates to a process for administering topically, orally, or parenterally to the host animal a larvicidally effective amount of a phenylene bis[imino(thio)-carbonyl]diphosphor(thio)amidic acid ester represented by formula:

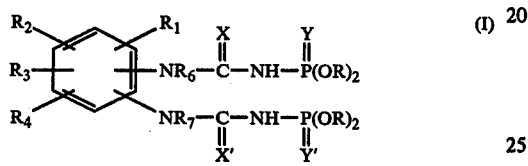

wherein R is hydrogen, alkyl $C_1$-$C_4$; $R_1$ is alkyl $C_1$-$C_4$, halogen, such as fluorine, chlorine, bromine, iodine, $R_5O$, $CF_3$, $F_5S(O)_n$; $R_2$, $R_3$, $R_4$ are each hydrogen, methyl or chloro; $R_5$ is alkyl $C_1$-$C_4$, benzyl, or phenyl; n is an integer from 0 to 2; $R_6$, $R_7$ are each hydrogen or alkyl ($C_1$-$C_4$); X, X', Y and Y' cannot all be O or all be S and X and X' each cannot both be oxygen when Y and Y' are both sulfur, and provided that $R_1$ cannot be methyl when $R_2$, $R_3$ and $R_4$ are each hydrogen or methyl.

In general, a preferred group of compounds for the control of said larvae and represented by formula (I) hereinabove defined are those wherein R is alkyl ($C_1$-$C_4$); $R_1$ represents a member selected from the group consisting of butyl, methoxy, benzyloxy, phenoxy, methylthio, n-propyl-thio, benzylthio, phenylthio, phenylsulfinyl, phenylsulfonyl, fluoro, chloro, bromo, iodo and $CF_3$; $R_2$ is hydrogen, methyl or chloro; $R_3$, $R_4$, $R_6$ and $R_7$ each are hydrogen; X, X', Y and Y' each are oxygen or sulfur, provided that X, X', Y and Y' cannot all be O or all be S, and X and X' cannot both be O when Y and Y' are both S.

The most preferred ortho isomers of formula (I) larvicidal compounds are those of the structure:

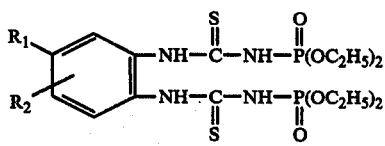

wherein $R_1$ is n-butyl, methoxy, benzyloxy, phenoxy, n-butyl-thio, benzylthio, phenylthio, phenylsulfinyl, phenylsulfonyl, fluoro, chloro, bromo, iodo or $CF_3$; $R_2$ is hydrogen, methyl or chloro.

The most preferred meta isomers of formula (I) larvicidal compounds are those of the structure:

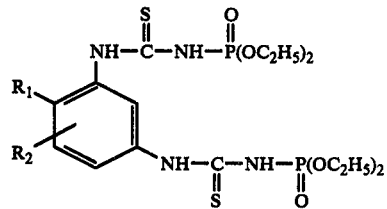

wherein $R_1$ is methoxy or chloro; and $R_2$ is hydrogen or methyl.

The most preferred para isomers of formula (I) larvicidal compounds are those of the structure:

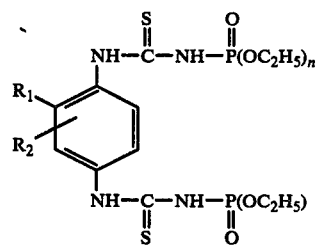

wherein $R_1$ is methoxy, phenoxy, methylthio, n-propylthio, benzylthio, phenylthio, fluoro, chloro, bromo, iodo or $CF_3$; $R_2$ is hydrogen, methyl or chloro.

As is known, certain tetraalkyl esters of {(o-phenylene)bis-[imino(thiocarbonyl)]}diphosphoramidic acid are disclosed in a Japanese patent application, the abstract of which has appeared in Chemical Abstracts at Volume 82, page 107520g. The application, Japanese-007108, filed 01/17/73, was published Sept. 5, 1974, No. 9093-541, filed by Ube Industries, Ltd., and assigned to the Institute of Physical and Chemical Research. The disclosed esters are said to be effective fungicidal agents. However, the compounds of the present invention are not described therein; nor is it anticipated or suggested that the above-said compounds would be effective for the control of the larvae of heel flies which parasitize ruminants and other warm-blooded animals.

It is further known that cattle grubs (or ox warbles) are the larvae of flies of the family Hypodermatidae, Genus Hypoderma, the heel flies. Of these, the best known species are: *Hypoderma lineatum*, the common cattle grub, and *Hypoderma bovis*, the northern cattle grub; the former is widely distributed on the North American Continent, Europe and Asia, while the latter is less widely distributed. The heel flies preferentially attach their eggs to the hairs on the legs of the host animal, in the area from hock to the knee if the animals are standing, but if the animal is bedded down, the eggs may be attached to hairs on other parts of the animal close to the ground. The eggs usually hatch within a week, and the newly hatched fly larvae bore directly into the skin or into hair follicles of the host animals. During the following 7 to 8 months, the larvae slowly migrate and burrow through the muscles and internal organs of the host animal and in time reach under the surface of the hide on the animal's back. Final development of the grubs takes place under the hide on the animal's back, where, the now rapidly developing grubs can be found in tumorous swellings which are provided with a breathing hole by said grubs. Thereafter, fully developed larvae emerge from the skin, drop to the ground and crawl into the loose earth where they pupate and finally emerge as warble flies.

As noted above, the life cycle of these parasites clearly indicates the damage caused by them. The infected host's internal organs and tissues are constantly irritated and damaged by the activity of the migrating larvae, often resulting in acute pain and sometimes even temporary paralysis. The afflicted animals may lose weight and might even die if the infestation is heavy.

Thus, the annual financial losses suffered by the cattle industry due to cattle grub infestations can be significant. These losses are in part due to loss of diseased animals, and in part due to damaged hides and depreciation in value of the carcass as flesh, since it becomes unfit as food.

Control of the cattle grubs is, therefore, highly desirable, especially in view of the fact that people engaged in caring for and handling cattle are also exposed to cattle grub infestations and if so infected would be subjected to the long-term debilitating effects of such infestations which, at times, may even lead to death.

It has been unexpectedly found that hereinabove defined, the compounds of formula (I), will control the larvae of heel flies in ruminants such as cattle, sheep and goats, and other warm-blooded animals, when administered topically, orally or parenterally to same in a single dose at dosage levels of from about 0.5 mg/kg to about 100 mg/kg of animal body weight and, preferably, between about 2.5 mg/kg and about 50 mg/kg, of animal body weight.

The said compounds can also be administered to animals on a continuing basis incorporated in the diet of the animals at drug levels between 0.006% and 0.2%, by weight, of the feed and, preferably, between 0.0125% and 0.05%, by weight, of the feed. For incorporation in the feed, the active compounds herein can be formulated as a premix or supplement containing from about 5% to 25%, by weight, of said compounds. The remainder of the premix or supplement is usually a mixture of animal nutrients, e.g. soybean meal, ground grain, corn meal, fermentation residues, vegetable oils and the like. The premix or supplement is added to the animal feed in sufficient quantity to provide a concentration of active compounds required for controlling the grub infection of said animals.

For single dose administration the compounds may be formulated as boluses, tablets, pills, injectables and the like, using pharmaceutically acceptable diluents, binders, lubricants, solvents and the like, e.g. dicalcium phosphate, starch, lactose, magnesium stearate, vegetable guns, isotonic saline solution and the like.

Formula (I) compounds may be administered topically from dilute aqueous solutions, emulsions or dipersions by spraying the host animals with same, or by immersing said animals into dip tanks containing the above formulations.

The larvicidal activity of the compounds of the invention may be conveniently evaluated by a method accepted by the U.S. Agricultural Research Service, in which mice infected with *Cuterebra spp.* are treated topically and/or orally with the compounds under evaluation.

Advantageously, the active phenylene bis[imino(thio)carbonyl]diphosphor(thio)amidic acid esters of the present invention can be prepared by reacting a mole of cyanatidate of the formula:

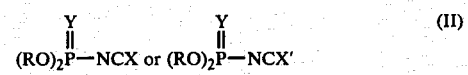

wherein R is alkyl ($C_1$–$C_4$) such as methyl, ethyl, n-propyl, isopropyl, n-butyl, or sec-butyl and X, Y, X' and Y' each represent sulfur or oxygen; with, a mole of o-,m- or p-phenylenediamine having the formula:

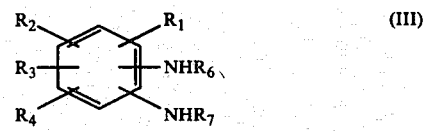

wherein $R_1$ is hydrogen, alkyl ($C_1$–$C_4$), fluorine, chlorine, bromine, iodine, $R_5O$, or $R_5O$, $CF_3$, or $R_5$-S-$(O)_n$—; $R_5$ is alkyl ($C_1$–$C_4$), benzyl or phenyl; $R_2$, $R_3$ and $R_4$ is each hydrogen, methyl or halo; $n$ is an integer from 0 to 2; and $R_6$ and $R_7$ are each hydrogen or alkyl ($C_1$–$C_4$). The reaction is conducted in the presence of an organic solvent at a temperature between about 0° C. and 100° C. The overall reaction can be illustrated as follows:

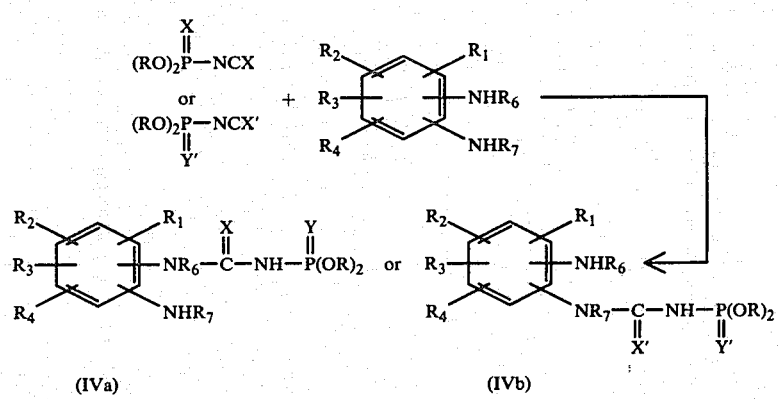

wherein R, $R_1$ to $R_4$, $R_6$, $R_7$, X, X', Y, Y' are as defined above.

The intermediate monophosphoramidate of formula (IVa) or (IVb) is then treated with a second mole of cyanatidate:

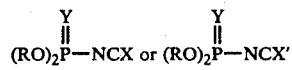

to yield the diphosphoramidate of formula (I) of the present invention in the above-mentioned manner and can be illustrated as follows:

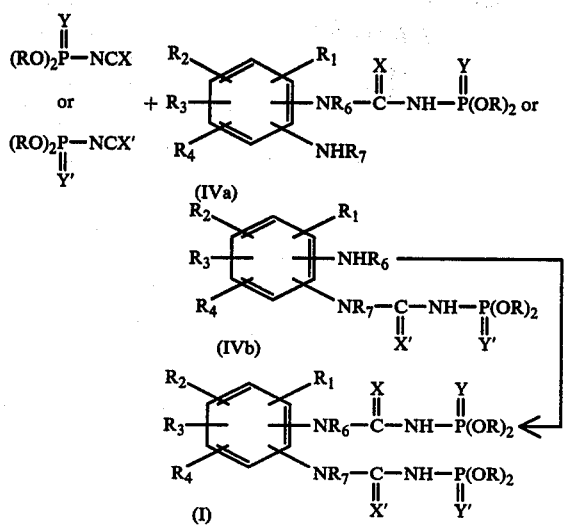

The reaction is preferably performed by the isolation of the intermediate monophosphoramidate (IVa) or (IVb) and then reacting (IVa) or (IVb) with a second mole equivalent or cyanatidate, whenever X is not equal to X' or Y is not equal to Y' in the desired diphosphoramidate (I).

Whenever X=X' and Y=Y' in the diphosphoramidate, (II), approximately two mole equivalents of the cyanatidate (II) are reacted with a mole equivalent of said phenylenediamine (III) at the onset of the reaction. The reaction is conducted in the presence of an organic solvent at a temperature between about 0° C. and 100° C. The overall reaction can be illustrated as follows:

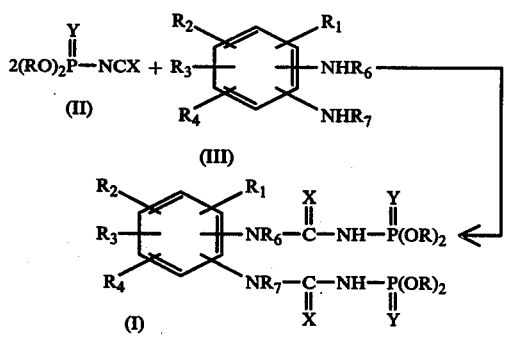

wherein R,R$_1$ to R$_4$,R$_6$,R$_7$,X,X',Y,Y' are as defined above.

Suitable solvents in which this reaction can be conducted include chlorinated hydrocarbons such as chloroform, methylene chloride and ethylene dichlorde; aromatics such as benzene and toluene; dialkyl or cyclic ethers, polyethers; nitriles such as acetonitrile and ketones such as acetone, diethylketone and the like.

The substituted phenylenediamine precursors, represented by formula III above, are prepared by known methods. For instance, 4-substituted phenylenediamines wherein R$_1$ is alkoxy(C$_1$-C$_4$) or alkylthio(C$_1$-C$_4$) are disclosed in a Belgium Application No. 821,176, published 4/17/75, or German Offenlegungsschrift No. 2,450,414, published 4/25/75, when R$_1$ is C$_6$H$_5$S, C$_6$H$_5$S→O, or C$_6$H$_5$SO$_2$, the preparation of the phenylenediamine (III) is disclosed in the Journal of Medicinal Chemistry, 18, 1164(1975); and, when R$_1$ represents the substituent R$_2$S→O, wherein R$_2$ is alkyl(C$_1$-C$_4$), the preparation of the phenylenediamine (III) is disclosed in U.S. Pat. No. 3,929,821, issued December 30, 1975. Finally, when R$_1$ represents phenoxy on the formula (III) phenylenediamine, the preparation of said phenylenediamine is disclosed in the South African Patent Application No. 72/907. Illustrative of other phenylenediamines are: 2-chloro-p-phenylenediamine, 4-chloro-o-phenylenediamine, 4-fluror-o-phenylenediamine, 4-methyl-o-phenylenediamine, 2-n-propylthio-p-phenylenediamine, 2-phenoxy-p-phenylenediamine, 4-n-propylsulfinyl-o-phenylenediamine, 4-n-propylsulfonyl-o-phenylenediamine, 4,5-dichloro-o-phenylenediamine, 6-chloro-m-phenylenediamine, 6-methyl-m-phenylenediamine, 4,5-dimethyl-o-phenylenediamine, 2,3,4,5-tetramethyl-o-phenylenediamine, 4-benzyloxy-o-phenylene, 4-n-butyl-o-phenylenediamine, N,N'-dimethyl-o-phenylenediamine, N-methyl-o-phenylenediamine, and equivalents thereof which are employed in these reactions.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of tetraethyl-{o-phenylene)bis[imino(thio)carbonyl]}diphosphoramidate A solution of 39.0 g of diethyl phosphoroisothiocyanatidate in 100 ml of chloroform is cooled in an ice bath. Into this cold solution is slowly stirred 10.8 g of o-phenylenediamine. A very mild exotherm is noted. The homogeneous dark brown solution is stirred for several minutes in the ice bath, and then is allowed to warm to room temperature. The solution then is heated at reflux for one our, cooled, and the solvent is evaporated under reduced pressure. The residual pasty solids (m.p. 123° to 127° C.) are suspended in ethyl acetate and filtered to yield 40.4 g (81%) of white crystals with m.p. 134.5°–135.5° C. (decomp.). Recrystallization from 300 ml of ethylene dichloride yields 32.5 g (65%) of large, colorless crystals with m.p. 135.5°–136.5° C. Infrared and proton magnetic resonance spectra confirm the indentity of the material.

Analysis: calculated for C$_{16}$H$_{28}$N$_4$O$_6$P$_2$S$_2$: C,38.55; H, 5.66; P, 12.43. Found: C, 38.72; H, 5.84; P, 12.12.

Substituting dimethyl phosphoroisothiocyanatidate or diisopropyl phosphoroisothiocyanatida te for diethyl phosphoroisothiocyanatidate in the reaction above, there are obtained tetra-methyl-{(o-phenylene)bis-[imino(thiocarbonyl)]}-diphosphoramidate, tetraisopropyl-{(o-phenylene)bis[imino-(thiocarbonyl)]}diphosphoramidate, respectively.

EXAMPLE 2

Preparation of Tetraethyl-{(4-substituted -o-phenylene)bis-[imino(thiocarbonyl)]}

The following compounds "A" are prepared by utilizing the method set forth in Example 1 above by replacing o-phenylenediamine with a 4-substituted-o- phenylenedi mine, the substituent ($R_1$) of which is defined below:

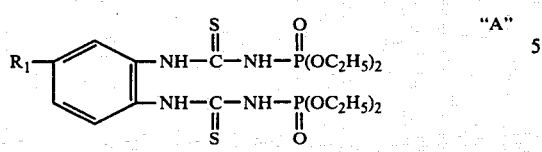

"A"

$CH_3O$, $C_2H_5O$, $N-C_3H_7O$, $i-C_3H_7O$, $n-C_4H_9O$, $t-C_4H_9O$, $i-C_4H_9O$, $CH_3S$, $C_2H_5S$, $n-C_3H_7S$, $2-C_3H_7S$, $n-C_4H_9S$, $C_6H_5CH_2S$, $C_6H_5CH_2O$, $C_6H_5O$, $C_6H_5S$, $C_6H_5S\ O$, $C_6H_5SO_2$, $CH_3S\ O$, $C_2H_5S\ O$, $n-C_3H_7S\ O$ $n-C_4H_9S\ O$, $C_6H_5CH_2S\ O$, $CH_3SO_2$, $n-C_3H_7\text{-}SO_2$, $n-C_4H_9SO_2$, $C_6H_5CH_2SO_2$.

EXAMPLE 3

Preparation of Tetraisopropyl-{(4-substituted-o-phenylene)-bis-[imino(thiocarbonyl)]}diphosphoramidates The following compounds "B" are prepared by the method if Example 1 by replacing diethylphosphinyl isothiocyanate with diisopropoxyphosphinyl isothiocyanate and using o-phenylenediamines with $R_1$ the substituent ($R_1$) of which in the 4-position is defined below:

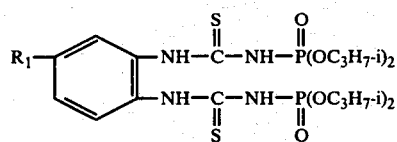

wherein $R_1$ is: Cl, Br, $CH_3$, $C_2H_5$, $i-C_3H_7$, $n-C_3H_7$, $n-C_4H_9$, $CH_3O$, $C_2H_5O$, $n-C_3H_7O$, $i-C_3H_7O$, $n-C_4H_9O$, $t-C_4H_9O$, $i-C_4H_9$-. $CH_3S$, $C_2H_5S$, $n-C_3H_7S$, $i-C_3H_7S$, $n-C_4H_9S$, $C_6H_5CH_2S$, $C_6H_5CH_2O$, $C_6H_5O$, $C_6H_5S$, $C_6H_5S\rightarrow O$, $C_6H_5SO_2$, $C_6H_5CH_2S\rightarrow O$, $CH_3S\rightarrow O$, $C_2H_5S\rightarrow O$, $n-C_3H_7S\rightarrow O$, $n-C_4H_9S\rightarrow O$, $CH_3SO_2$, $n-C_4H_9SO_2, C_6H_5CH_2\ SO$

EXAMPLE 4

Preparation of Tetramethyl-{(4-substituted-o-phenylene)bis-[imino(-thiocarbonyl)]$^5$}diphosphoramidates The following compounds "C" are prepared by the method of Example 1 by replacing o-phenylenediamine with 4-substituted-o-phenylenedimines, the substituent of which ($R_1$) in the 4-position is defined below as:

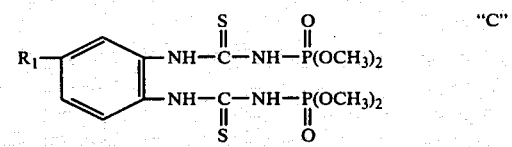

"C"

wherein $R_1$ is cl, Br, $CH_3$, $C_2H_5$, $i-C_3H_7$, $n-C_3H_7$, $n-C_4H_9$, $CH_3O$, $C_2H_5O$, $n-C_3H_7O$, $i-C_3H_7O$, $n-C_4H_9O$, $t-C_4H_9O$, $CH_3S$, $C_2H_5S$, $n-C_3H_7S$, $2-C_3H_7S$, $n-C_4H_9S$, $C_6H_5CH_2S$, $C_6H_5CH_2O$, $C_6H_5O$, $C_6H_5S$, $C_6H_5S\rightarrow O$, $C_6H_5SO_2$, $CH_3S\rightarrow O$, $C_2H_5S\rightarrow O$, $n-C_3H_7S\rightarrow O$, $n-C_4H_9S\rightarrow O$, $C_6H_5CH_2S\rightarrow O$, $CH_3SO_2$, $n-C_3H_7SO_2$, $n-C_4H_9SO_2$, $C_6H_5CH_2SO_2$.

EXAMPLE 5

The following compounds "D" are prepared by the method of Example 1, wherein an appropriate isocyanate or isothiocyanate,

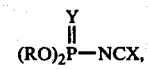

$(RO)_2P-NCX$, is caused to react with phenylenediamine utilizing toluene in lieu of chloroform to recover a white solid in good yield.

| "D" Product | m.p. (in °C) |
|---|---|
| $(C_2H_5O)_2\overset{O}{\underset{\|}{P}}-NH-\overset{S}{\underset{\|}{C}}-NH-\underset{}{\text{[phenyl]}}-NH-\overset{S}{\underset{\|}{C}}-NH-\overset{O}{\underset{\|}{P}}(OC_2H_5)_2$ | 147-149 |
| $(C_2H_5O)_2\overset{O}{\underset{\|}{P}}-NH-\overset{S}{\underset{\|}{C}}-NH-\underset{}{\text{[phenyl]}}-NH-\overset{S}{\underset{\|}{C}}-NH-\overset{O}{\underset{\|}{P}}(OC_2H_5)_2$ | 143-145 |
| $Cl-\text{[phenyl]}-NH-\overset{S}{\underset{\|}{C}}-NH-\overset{O}{\underset{\|}{P}}(OC_2H_5)_2$ / $-NH-\overset{C}{\underset{\|\ \ \|}{S}}-NH-\overset{}{\underset{O}{P}}(OC_2H_5)_2$ | 144-146 |
| $C_6H_5-S-\text{[phenyl]}-NH-\overset{S}{\underset{\|}{C}}-NH-\overset{O}{\underset{\|}{P}}(OC_2H_5)_2$ / $-NH-\overset{C}{\underset{\|\ \ \|}{S}}-NH-\overset{}{\underset{O}{P}}(OC_2H_5)_2$ | 98-100 |

-continued
| "D" Product | m.p. (in ° C) |
|---|---|
| 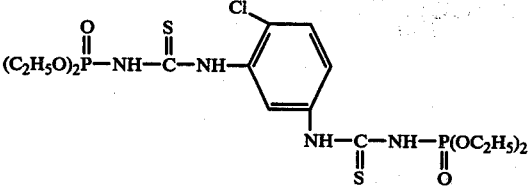 | 138–139 |
| 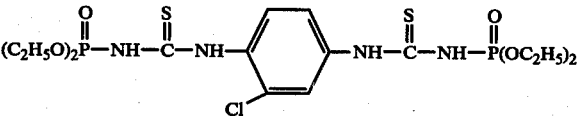 | 148–149 |
| 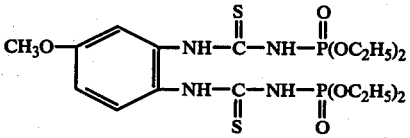 | 144–146 |
| 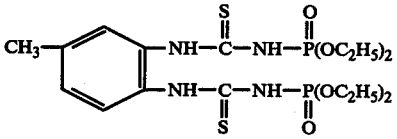 | 139–141 |
| 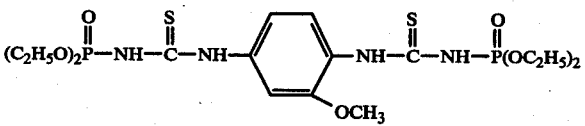 | 143–144 |
| 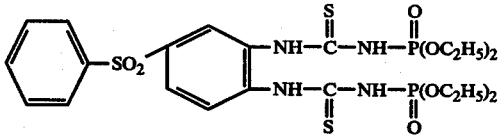 | 142–143 |
| 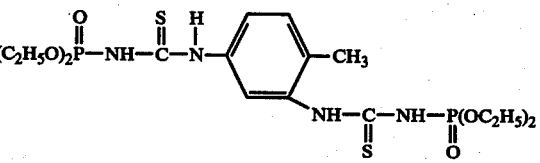 | 132–133 |
| 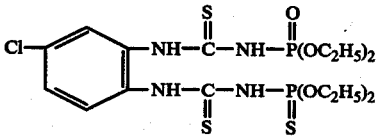 | 125–127 |
| 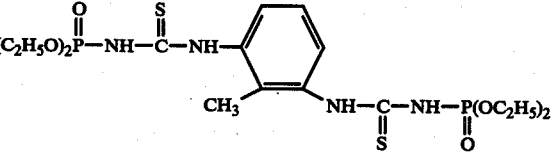 | 155–156 |
| 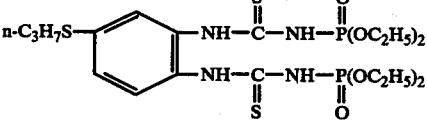 | 95–97 |

| "D" Product | m.p. (in °C) |
|---|---|
| 3,4-dichlorophenyl bis[NH-C(=S)-NH-P(=O)(OC₂H₅)₂] | 168-169 |
| phenyl-1,2-bis[NH-C(=S)-NH-P(=O)(O-CH(CH₃)₂)₂] | 134-141 |
| 4-(phenylsulfinyl)phenyl-1,2-bis[NH-C(=S)-NH-P(=O)(OC₂H₅)₂] | 123-125 |
| 4-fluorophenyl-1,2-bis[NH-CS-NH-P(=O)(OC₂H₅)₂] | 148-150 |
| 4,5-dimethylphenyl-1,2-bis[NH-CS-NH-P(=O)(OC₂H₅)₂] | 143-146 |
| 3,4,5,6-tetramethylphenyl-1,2-bis[NH-CS-NH-P(=O)(OC₂H₅)₂] | 185-188 |
| 4-methylphenyl-1,2-bis[NH-CS-NH-P(=O)(OC₃H₇-i)₂] | 134-141 |
| 3-methylphenyl-1,4-bis[NH-CS-NH-P(=O)(OC₂H₅)₂] | 156.5-157.5 |
| 2-methoxyphenyl-1,4-bis[NH-CS-NH-P(=O)(OC₂H₅)₂] | 125-126 |

| "D" Product | m.p. (in °C) |
|---|---|
| 4-benzyloxy-phenyl bis(thiourea-N'-diethylphosphate) | 123–126 |
| 2-(n-propylthio)-phenyl bis(thiourea-N'-diethylphosphate) | 126–129 |
| 2-(phenylthio)-phenyl bis(thiourea-N'-diethylphosphate) | 141–143 |
| 2-phenoxy-phenyl bis(thiourea-N'-diethylphosphate) | 130–133 |
| 3,4-dimethyl-phenyl bis(thiourea-N'-diethylphosphate) | 150–153 |
| 4-bromo-phenyl bis(thiourea-N'-diethylphosphate) | 140–141 |
| 2,4-dichloro-phenyl bis(thiourea-N'-diethylphosphate) | 146–147 |
| 2,4-dimethyl-phenyl bis(thiourea-N'-diethylphosphate) | 146–147 |

-continued
| "D" Product | m.p. (in °C) |
|---|---|
| 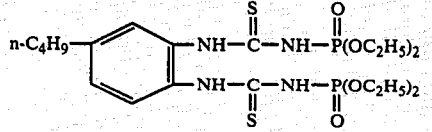 | 60–85 |
| 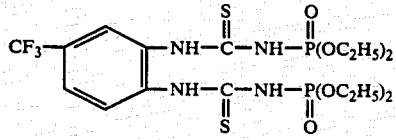 | — |
| 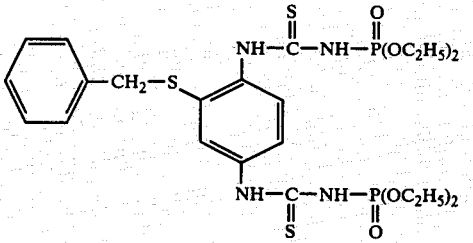 | 129–133 |
| 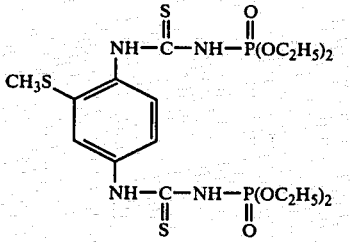 | 138–141 |
| 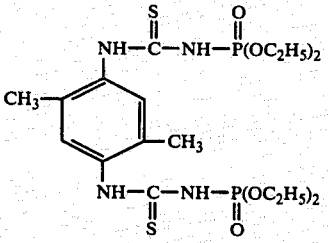 | 167–168 |
| 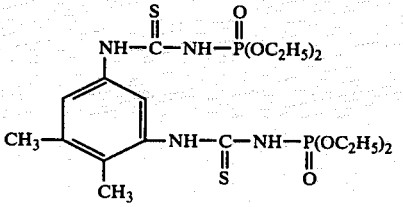 | 129–131 |
| 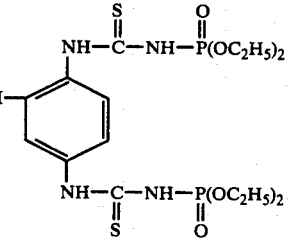 | 149–150 |

| "D" Product | m.p. (in °C) |
|---|---|
| 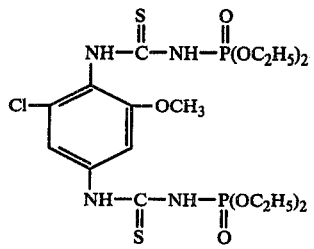 | 148–151 |
| 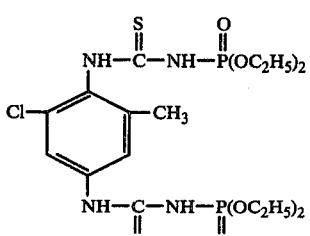 | 152–155 |
| 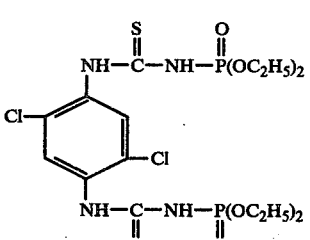 | 164–165 |
| 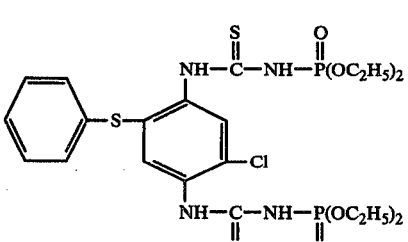 | 143–146 |
| 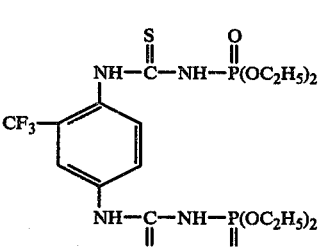 | 151–152 |
| 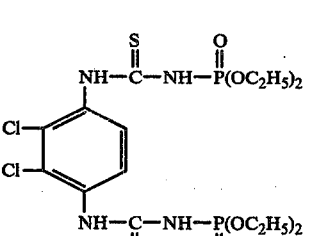 | 150–153 |

| "D" Product | m.p. (in °C) |
|---|---|

Structure 1: 2-chloro-1,4-phenylene bis[NH-C(=S)-NH-P(=O)(OC₃H₇-i)₂] — m.p. —

Structure 2: 2-methoxy-1,4-phenylene bis[NH-C(=S)-NH-P(=O)(OC₃H₇-i)₂] — m.p. —

Structure 3: 2-(n-C₃H₇S)-1,4-phenylene bis[NH-C(=S)-NH-P(=O)(OC₂H₅)₂] — m.p. —

Structure 4: 2-(n-C₃H₇S)-5-Cl-1,4-phenylene bis[NH-C(=S)-NH-P(=O)(OC₂H₅)₂] — m.p. 133–134

Structure 5: 2-Cl-5-(n-C₃H₇S)-1,4-phenylene bis[NH-C(=S)-NH-P(=O)(OC₂H₅)₂] — m.p. 134–137

Structure 6: 2-Cl-3-CH₃O-1,4-phenylene bis[NH-C(=S)-NH-P(=O)(OC₂H₅)₂] — m.p. 142–145

| "D" Product | m.p. (in °C) |
|---|---|

-continued

Structure 1: 4-CH₃O, 2-Cl phenyl with two NH-C(=S)-NH-P(=O)(OC₂H₅)₂ groups (1,4-positions) — —

Structure 2: 4-CH₃O, 2-CH₃ phenyl with two NH-C(=S)-NH-P(=O)(OC₂H₅)₂ groups (1,4-positions) — —

Structure 3: 2,3-dimethyl phenyl with two NH-C(=S)-NH-P(=O)(OC₂H₅)₂ groups (1,4-positions) — —

Structure 4: 2,6-dimethyl phenyl with two NH-C(=S)-NH-P(=O)(OC₂H₅)₂ groups (1,4-positions) — —

Structure 5: 2-CH₃O phenyl with two NH-C(=S)-NH-P(=O)(OC₃H₇-i)₂ groups (1,4-positions) — —

Structure 6: 2-Br phenyl with two NH-C(=S)-NH-P(=O)(OC₂H₅)₂ groups (1,4-positions) — —

EXAMPLE 6

Preparation of
Tetraethyl-{[(2-chloro-5-phenylthio)-p-phenylene]bis-[imino(thiocarbonyl)]}diphosphoramidate A solution of 2-chloro-5-phenylthio-p-phenylenediamine (7.8 g) in methylene chloride (16 ml) is stirred and 26 ml of a solution of

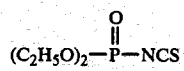

in methylene chloride (195 g in 350 ml of methylene chloride) is added. The mixture is heated at reflux for one hour, then evaporated to dryness and the residue warmed at 50° C. for two hours. Acetone (60 ml) is added to the residue and the mixture is stirred and after a period of time, a white precipitate is formed. The mixture is then diluted with pentane (30 ml), the solid collected and washed with acetone, to afford 10.4 g of title compound, m.p. 143°–144° C.

Similarly, the following compounds are prepared using the appropriately substituted diamines:

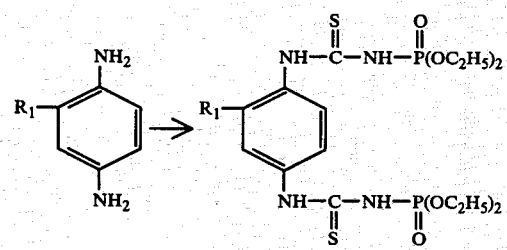

wherein $R_1$ is $CH_3S$, $C_2H_5S$, $i-C_3H_7S$, $n-C_4H_9S$, benzylthio, phenylthio, F, $C_2H_5O$, $n-C_3H_7O$, $n-C_4H_9O$, benzyloxy, phenoxy, $C_2H_5$ and $n-C_4H_9$.

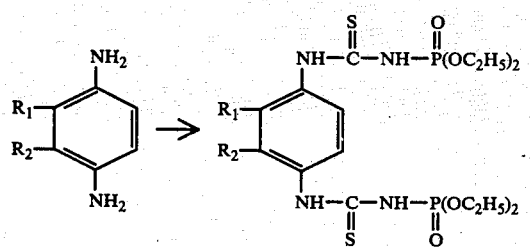

wherein $R_1$ is Cl; and $R_2$ is Cl, $CH_3O$, $C_2H_5O$, $n-C_3H_7O$, $n-C_4H_9O$, phenoxy, benzyloxy, $CH_3S$, $C_2H_5S$, $n-C_3H_7S$, $n-C_4H_9S$, phenylthio or benzylthio.

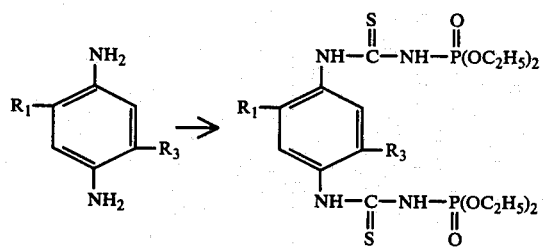

wherein $R_3$ is Cl; $R_1$ is $CH_3S$, $C_2H_5S$, $n-C_3H_7S$, $n-C_4H_9S$, benzylthio, $CH_3O$, $C_2H_5O$, $N-C_3H_7O$, $i-C_3H_7O$, $n-C_4H_9O$, benzyloxy and phenoxy.

EXAMPLE 7

Preparation of
O,O-Diethyl(2-aminophenyl)thiocarbamoylphosphoramidothioate

A mixture of 10.8 g of o-phenylenediamine and 350 ml of dry toluene is cooled to 0° C. under nitrogen. A solution of 23.8 g (18.74 ml) of freshly distilled diethoxyphosphinylisothiocyanate and 20 ml of toluene is added dropwise with stirring. After addition of the isothiocyanate is complete, the mixture is warmed to ambient temperature and stirred for 10 hours and then warmed to 45° C. and stirred for 48 hours to complete the reaction. The mixture is cooled to 20° C. and filtered to yield the title compound as a pale, grey solid which is washed with two 50-ml portions of ether. (20.3g); 64% yield). The product is homogeneous on thin layer chromotography (tlc) and has a melting point of 106.0° C. to 107.0° C.

EXAMPLE 8

Preparation of
Diethyl(o-[3-(diethoxyphosphinothioyl)phenyl]-thiocarbamoylphosphoramidate.

A sample of 20.0 g (0.065 moles) of O,O-diethyl(2-aminophenyl)thiocarbamoylphosphoramidothioate is suspended in 200 ml of dry toluene at 0° C. under a nitrogen atmosphere. A solution of about 0.069 moles of diethoxyphosphinyl isothio cyanate is dry toluene is added dropwise with stirring. When addition is complete, the mixture is warmed to ambient temperature and stirred for 24 hours. It is then stirred at 45° C. 24 hours.

The mixture is concentrated in vacuo to a volume of about 100 ml and diluted with 50 ml of anhydrous ether. The mixture is cooled 2 hours at 0° C. and then filtered to yield 25.2 g of the title compound as a slightly grey powder. The material is purified by stirring as a slurry in warm toluene and cooling on ice. The mixture is filtered to yield 21.6 g of pure product as a slightly grey solid with a melting point of 135.0° C. to 137.0° C.

EXAMPLE 9

Preparation of Diethoxyphosphinyl Isothiocyanate

To a mixture of 8.02 g of dry sodium thiocyanate in 100 ml of dry toluene at 0° C., under a nitrogen atmosphere is added 13.1 ml (16.6 g) of diethyl phosphorchloridate dropwise with stirring. The mixture is warmed to ambient temperature and stirred 20 hours. The mixture is filtered through a pad of Celite and the pad is washed with two 50 ml portions of toluene. The filtrate is washed with 50 ml of ice cold 10% sodium bicarbonate solution, 50 ml of ice water and dried over anhydrous magnesium sulfate. The mixture is filtered and the filtrate used without further purification in subsequent reaction.

EXAMPLE 10

Preparation of Diethoxythiophinothioyl Isothiocyanate

To a mixture of 33.2 g of dry sodium thiocyanate and 300 ml of dry, spectral grade acetonitrile at 0° C. is added 85 ml of diethyl phosphochloridate dropwise, with stirring in a nitrogen atmosphere. The mixture is warmed to ambient temperature and stirred 48 hours. The mixture is filtered through Celite and the filtrate concentrated in vacuo to give an oily liquid. The liquid is distilled under reduced pressure to give 490 g of pure product. The boiling point is 45.0° C./0.15 mm.

EXAMPLE 11

Employing the method of Example 10, the following compounds are prepared by substituting either o-phenylenediamine or diethoxyphosphinyl isothiocyanate with the appropriate o or m p-phenylenediamine or dialkoxyphosphinyl isothiocyanage or dialkoxyphosphinyl isocyanate to afford the intermediate; dialkyl (o or m-amino substituted phenylthiocarbamoylphosphoramidothioate.

| Compound | mp° C |
|---|---|
| [phenyl]-NH—CS—NH—PO(OC$_2$H$_5$)$_2$ with NH$_2$ | 122–125 |
| H$_2$N—[phenyl]—NH—CS—NH—PS(OC$_2$H$_5$)$_2$ | 128–130 |
| Cl—[phenyl]—NH—CS—NH—PO(OC$_2$H$_5$)$_2$ with NH$_2$ | 130–133 |
| Cl,Cl—[phenyl]—NH—CS—NH—PO(CO$_2$H$_5$)$_2$ | 165–167 |
| Cl—[phenyl]—NH—CS—NH—PS(OC$_2$H$_5$)$_2$ with NH$_2$ | 120–121 |
| O$_2$N—[phenyl]—NH—CS—NH—PO(OC$_2$H$_5$)$_2$ with NH$_2$ | 144–146 |
| [phenyl]—NH—CS—NH—PO(OC$_2$H$_5$)$_2$ with O$_2$N, NH$_2$ | 137–139 |
| Cl, H$_2$N, Cl—[phenyl]—NH—CS—NH—PO(OC$_2$H$_5$)$_2$ | 145–148 |
| [phenyl]—NH—CO—NH—PO(OC$_2$H$_5$)$_2$ with NH$_2$ | 147–152 |
| [phenyl]—NH—CO—NH—PS(OC$_2$H$_5$)$_2$ with NH$_2$ | 133–136 |
| [phenyl]—NH—C(S)—NH—PO(OC$_2$H$_5$)$_2$ with NH$_2$ | 100–103 |

EXAMPLE 12

Preparation of Diethoxyphosphinothioyl isothiocyanate

A mixture of 97.2 g of dry potassium isothiocyanate and 188.6 g of 0,0,-diethyl thiophosphoryl chloride in 500 ml of CH$_3$CN is stirred at 65° C. for 4 hours and then at reflux for 1.5 hours. The solvent is evaporated at reduced pressure and the residue is dissolved in benzene. The benzene solution is washed twice with brine, dried over magnesium sulfate, and evaporated. The residue is distilled at 70°–72°/0.38 Torr to afford the title compound, $n_D^{25}$ 1.5293.

Similarly, substituting 0,0-diethyl thiophosphoryl chloride with 0,0-diisopropyl thiophosphoryl chloride in the above procedure affords diisopropoxyphosphinothioyl isothiocyanate, while substitution with 0,0-dibutylthiophosphoryl chloride affords dibutoxyphosphinothioyl isothiocyanate.

EXAMPLE 13

Preparation of Diethoxyphosphinyl isothiocyanate

The title compound is prepared by the method of M. Kulka [Canadian Journal of Chemistry, 37, 525(1959)] by allowing diethylphosphorchloridate and ammonium thiocyanate to react in benzene; b.p. 76° C. to 83° C./0.5 Torr; $n_D^{25}$ 1.4758.

Similarly, diisopropoxyphosphinyl isothiocyanate, dimethoxyphosphinyl isothiocyanate, dibutylphosphinyl isothiocyanate and dipropoxphosphinyl isothiocyanate are prepared.

EXAMPLE 14

Preparation of Dimethoxyphosphinothioyl isocyanate

The title compound is prepared according to the method of L. I. Samaraj, O. I. Kolodjaznij, and G. I. Derkatsch [Angewandte Chemie International Edition, 1, 618(1968)]

Similarly, diethoxyphosphinothioyl isocyanate, diisopropoxyphoshinothioyl isocyanate, dimethoxyphosphinyl isocyanate, diethoxyphosphinyl isocyanate, dipropoxyphosphinyl isocyanate, dibutylphosphinyl isocyanate and diisopropoxyphosphinyl isocyanate are prepared.

The following are exemplary of the preparation of certain aniline intermediates useful in the preparation of the compounds of the present invention.

EXAMPLE 15

Preparation of 4-Nitro-3-(n-propylthio)aniline

In 50 ml of dry dimethylformamide, 5 grams of 3-chloro-4-nitroaniline, 6.9 grams of potassium carbonate, and 2.73 ml of n-propyl mercaptan are stirred under nitrogen atmosphere for 5 minutes and then heated at 87° C. for 20.5 hours. An additional 0.5 ml of propyl mercaptan is then added and the mixture is heated 2 hours at 105° C. The mixture is cooled, poured into 400 ml of $H_2O$ with stirring to afford the gold-colored product (6 grams), melting at 68°–72° C.

EXAMPLE 16

Preparation of 3-Methylthio-4-nitroaniline

A mixture of dry dimethylformamide (150 ml) and potassium carbonate (12.0 g) is stirred and methyl mercaptan is introduced as a gas for 45 minutes. After stirring for another 45 minutes, 3-chloro-4-nitroaniline (10.0 g) is added. The mixture is stirred and heated at 120°–130° C. for 18 hours. It is then cooled and poured into water (1 liter), the precipitate is collected and recrystallized from methanol to afford 8 grams of 3-methylthio-4-nitroaniline, m.p. 178°–182° C.

Similarly, 3-ethylthio-4-nitroaniline, 3-n-propylthio-4-nitroaniline, 3-isopropylthio-4-nitroaniline, 3-n-butylthio-4-nitroaniline and 3-benzylthio-4-nitroaniline are each prepared employing the corresponding mercaptan in excess.

EXAMPLE 17

In a Paar hydrogenation bottle, 7 g of 4-nitro-3(n-propylthio)aniline, 7 g of 5% Palladium/carbon, and 5.32 ml of concentrated hydrochloric acid in 200 ml of absolute ethanol are shaken under 3.36 $kg/cm^2$ pressure for 50 minutes (2.80 $kg/cm^2$ pressure). The mixture is filtered through Celite and the filter cake is washed with 150 ml of ethanol. The combined wash and filtrate is evaporated to dryness in vacuo to afford a white solid, which is stirred in 50 ml of cold acetone and collected to yield 5.2 g of n-propylthio-p-phenylenediamine (m.p. 213°–225° C.).

EXAMPLE 18

Preparation of 2-Methylthio-p-phenylenediamine

In a Paar hydrogenation bottle, a mixture of 3-methylthio-4-nitroaniline (7.7 g), 5% Pd/C catalyst (8.0 g), concentrated hydrochloric acid (7 ml) and ethanol (200 ml) is treated with hydrogen at 3.43 $kg/cm^2$ for 45 minutes (until 0.8 $kg/cm^2$ hydrogen is absorbed). The mixture is filtered through diatomaceous earth and the filtrate evaporated to dryness afford 3-methylthio-p-phenylenediamine hydrochloride. The salt is dissolved in water, the solution made alkaline (pH 9–10) with 50% sodium hydroxide and the diamine extracted with methylene chloride (3×150 ml). The combined extracts are dried over magnesium sulfate and evaporated to dryness to afford 4.75 g of title product, a brown solid, which is used as is.

In the same manner, 3-ethylthio-, 3-n-propylthio-, 3-isopropylthio-, 3-n-butylthio- and 3-benzylthio-4-nitroan-iline are reduced to afford 2-ethylthio-, 2-n-propylthio-, 2-isopropylthio-, 2-n-butylthio and 2-benzylthio-p-phenylene-diamine, respectively, in good yield.

EXAMPLE 19

Preparation of 2-Iodo-4-nitroaniline

A solution of iodine monochloride (23.54 g) in acetic acid (50 ml) is added dropwise over an hour to a stirred solution of p-nitroaniline (20 g). After stirring for another hour, the dark mixture is poured into water (1 liter), the precipitated yellow solid is collected and dried to afford 41.15 g title product, m.p. 90°–95° C.

EXAMPLE 20

Preparation of 2-Iodo-p-phenylenediamine

A mixture of concentrated hydrochloric acid (150 ml) and 2-iodo-4-nitroaniline (30.0 g) is stirred and warmed to 45°–50° C. A solution of stannous chloride dihydrate (90.0 g) in concentrated hydrochloric acid (110 ml) is added while maintaining the reaction temperature at 65°–70° C. After the addition is completed, the mixture is cooled in an ice bath and 50% sodium hydroxide (250ml) is added slowly. The mixture is filtered and the isolated damp solid is stirred in 600 ml water at reflux. The solution is decolorized with charcoal, filtered and cooled to afford 5.55 g of title compound, m.p. 95°–99° C.

EXAMPLE 21

Preparation of 2-Chloro-4-nitro-6-methoxyaniline

A mixture of concentrated hydrochloric acid (250ml), water (250 ml) and 2-methoxy-4-nitroaniline (48.76 g) is stirred at 47° C. and 30% hydrogen peroxide (30 ml) is added. The temperature is kept at 50°–62° C. and after one hour an additional 125 ml of concentrated hydrochloric acid and 15 ml of 30% hydrogen peroxide are added. After 45 minutes at 45°–48° C., the mixture is cooled and the precipitate collected to yield 54 g of a brown solid. This material is purified by dry column chromatography using silica and 1:1 hexane/toluene eluent to afford 11.0 g of title product, m.p. 114°–11–° C.

Similarly, 2-chloro-4-nitro-6-methylaniline, m.p. 154°–159° C., is prepared from 2-methyl-4-nitroaniline.

Using the corresponding 6-alkyl-4-nitroaniline, the following are also prepared: 2-chloro-4-nitro-6-ethylaniline and 2-chloro-4-nitro-6-n-butylaniline.

EXAMPLE 22

Preparation of 2,3-Dichloro-4-nitroaniline

A solution of 2,3-dichloroaniline (162.0 g) in p-toluenesulfonyl chloride (190.7 g) is heated at 100° C. for one hour allowing the temperature to rise to 115° C. with the exotherm. The thick mixture is then cooled to 50° C. and pyridine (250 ml) is added carefully. The reaction mixture exotherms to 150° C. After stirring for one hour the mixture is cooled and poured into water (2.5 liter). The precipitated solid is collected and dried to yield 301 g of tosylamide, m.p. 112°–118° C.

The tosylamide (250 g) is added to 70% nitric acid (71.15 g) and the mixture warmed on a steam bath and is cooled after the evolution of red fumes stops. The mixture is then stirred with 1 liter of water and the solid collected. The nitrated product is recrystallized from methanol to afford 137.2 g solid, m.p. 139°–144° C. This crude product is dissolved in concentrated sulfuric acid (150 ml) and the solution warmed on a steam bath for 35 minutes. The solution is cooled and poured into two liters of water, the precipitate is collected and dried to afford 77.1 g of title compound, m.p. 170°–174° C.

EXAMPLE 23

Preparation of 2-Chloro-3-methoxy-4-nitroaniline

A solution of 2,3-dichloro-4-nitroaniline (25 g) and sodium methoxide (25 g) in methanol (250 ml) is stirred and heated at reflux under a nitrogen atmosphere for 5.5 hours. The reaction mixture is poured into water (1.5 l), the precipitated yellow solid is collected and dried. This material is purified by chromatography on silica gel using 1:1 hexane/ether eluent. The eluents are collected and evaporated to dryness to afford 13 g of title compound, m.p. 118°–123° C.

Similarly, 2,5-dichloro-4-nitroaniline is allowed to react with methoxide ion to afford 2-chloro-4-nitro-5-methoxyaniline, m.p. 150°–152° C. Also by allowing 2,3-dichloro-4-nitroaniline to react with sodium ethoxide, sodium propoxide, sodium butoxide and sodium benzyloxide, 3 ethoxy-, 3-propoxy-, 3-isopropoxy-, 3-butoxy- and 3-benzyloxy-4-nitroaniline are obtained.

Reaction of 2,5-dichloro-4-nitroaniline with the above alkoxides in the same manner also affords 5-ethoxy-, 5-propoxy-, 5-isopropoxy-, 5-n-butoxy-, and 5-benzyloxy-2-chloro-4-nitroaniline.

EXAMPLE 24

Preparation of 2-Chloro-4-nitro-5-phenoxyaniline

A mixture of 2,5-dichloro-4-nitroaniline (7.0 g), phenol (3.2 g), potassium carbonate (9.7 g) and dry dimethylformamide (50 ml) is stirred and heated at 100° C. for 7.5 hours. The mixture is then poured into 500 ml of ice water and stirred. The aqueous mixture is extracted with ethyl acetate (5×200 ml), the extracts are dried and evaporated to dryness. The residual oil is stirred with methylene chloride (20 ml), the resulting solid is collected and dried to yield 3.5 g of title product, m.p. 122°–124° C.

Similarly, 2.5-dichloro-4-nitroaniline is allowed to react with n-propyl mercaptan and thiophenol in dimethylformamide at 100° C. in the presence of potassium carbonate to afford 2-chloro-4-nitro-5-n-propylthioaniline, m.p. 125°–127° C., and 2-chloro-4-nitro-5-phenylthioaniline, m.p. 163°–166° C.

Also in the above described manner the following products are prepared:

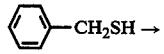

| Starting material | Mercaptan | Product |
| --- | --- | --- |
| 2,5-dichloro-4-nitroaniline | CH$_3$SH → | 2-Chloro-4-nitro-5-methylthioaniline |
| | C$_2$H$_5$SH → | 2-Chloro-4-nitro-5 ethylthioaniline |
| | n-C$_4$H$_9$SH → | 2-Chloro-4-nitro-5-butylthioaniline |
| | ⌬-CH$_2$SH → | 2-Chloro-4-nitro-5-benzylthioaniline |
| 2,3-dichloro-4-nitroaniline | CH$_3$SH → | 2-Chloro-3-methylthio-4-nitroaniline |
| | C$_2$H$_5$SH → | 2-Chloro-3-ethylenethio-4-nitroaniline |
| | n-C$_3$H$_7$SH → | 2-Chloro-3-propylthio-4-nitroaniline |
| | n-C$_4$H$_9$SH → | 2-Chloro-3-n-butylthio-4-nitroaniline |
| | thiophenol → | 2-Chloro-3-phenylthio-4-nitroaniline |

-continued

| Starting material | Mercaptan | Product |
| --- | --- | --- |
| | ⌬-CH$_2$SH → | 2-Chloro-3-benzylthio-4-nitroaniline- |

EXAMPLE 25

Preparation of 2-chloro-5-n-propylthio-p-phenylenediamine

A mixture of 2-chloro-4-nitro-5-n-propylthioaniline (7.0 g) and concentrated hydrochloric acid (40 ml) is warmed to 65°–75° C. and a solution of stannous chloride dihydrate (30 g) in concentrated hydrochloric acid (40 ml) is added dropwise. After 2.5 hours, the mixture is cooled and 50% aqueous sodium hydroxide (80 ml) is added. The mixture is extracted with 1 liter methylene chloride, the extract dried over magnesium sulfate and evaporated to dryness to afford 4.8 g of product, a brown oil, which is used in subsequent reactions without further purification.

Similarly, 2-chloro-4-nitro-5-phenoxyaniline is reduced to give 2-chloro-5-phenoxy-p-phenylenediamine, 2-chloro-4-nitro-5-phenylthioaniline to give 2-chloro-5-phenylthio-p-phenylenediamine, 2-chloro-4-nitro-5-methoxyanilino to give 2-chloro-5-methoxy-p-phenylenediamine, and 2,5-dichloro-4-nitroaniline to give 2,5-dichloro-p-phenylenediamine.

The above procedure is also used to prepare the following phenylenediamines, wherein the starting nitroanilines are described above.

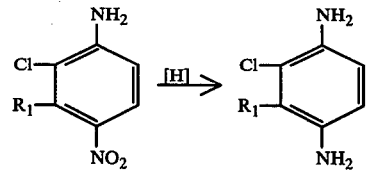

wherein R$_1$ is CH$_3$S, C$_2$H$_5$S, n-C$_3$H$_7$S, n-C$_4$H$_9$S, phenylthio, benzylthio, CH$_3$O, C$_2$H$_5$O, n-C$_3$H$_7$O, 3-i-C$_3$H$_7$O, n-C$_4$H$_9$O, phenoxy and benzyloxy;

and

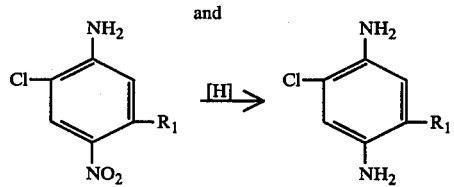

wherein R$_1$ is CH$_3$S, C$_2$H$_5$S, n-C$_4$H$_9$S, benzylthio, CH$_3$O, C$_2$H$_5$O, n-C$_3$H$_7$O, i-C$_3$H$_7$O, n-C$_4$H$_9$O and benzyloxy.

EXAMPLE 26

Preparation of 2-n-Propoxy-p-phenylenediamine

A mixture of 2,5-dinitrophenol (10 g), potassium carbonate (15 g) and acetone (100 ml) is stirred and n-propyl bromide (13.36 g) added to the mixture. The mixture is stirred at room temperature for 3 hours and then heated at reflux for 16 hours. More n-propyl bromide (6.68 g) is then added and refluxing continued for 96 hours. The mixture is filtered and the filtrate evaporated to dryness to afford a dark brown solid. This material is stirred with water (300 ml) and filtered. Recrystallization from methanol yields 8.9 g of 1-n-propoxy-2,5-dinitrobenzene, m.p. 52°–54° C. This compound (8.4 g) is reduced with hydrogen in a pressure vessel in the presence of methanol (250 ml) and 5% Pd/C catalyst (0.85 g) starting pressure: 3.36 kg/cm$^2$, final pressure: 2.52 kg/cm$^2$. The mixture is filtered and evaporated to dryness to afford 6.1 g of oily title compound, which is used in subsequent reactions without further purification.

Similarly, 2-n-butoxy-p-phenylenediamine, 2-ethoxy-p-phenylenediamine are prepared using butyl iodide and ethyl iodide in the first step. Use of benzyl bromide affords 2-benzyloxy-p-phenylenediamine.

EXAMPLE 27

Preparation of Tetraethyl-{[4-(phenylthio)-o-phenylene]bis[imino(thiocarbonyl)]}diphosphoroamidate A 0.01 mole sample of diethoxyphosphinyl isothiocyanate is stirred in toluene in an ice bath and 1 g of 4-phenylthio-o-phenylenediamine in dry toluene is added dropwise. The mixture is then allowed to warm to room temperature and stirred for 16 hours. The mixture is poured into H$_2$O and extracted with toluene. The extracts are dried and evaporated to dryness. The residual oil is dissolved in 10 ml of CHCl$_3$ and chromatographed on a FLOROSIL ® column using Et$_2$O as eluent. Two fractions, m.p. 69° C. to 72° C. and m.p. 70° C. to 72° C., are obtained. Recrystallization from acetone/Et$_2$O/hexane affords the title compound, m.p. 70° C. to 72° C.

EXAMPLE 28

Evaluation of the Efficacy the above-defined Diphosphoramidate Compounds for the control of Cuterebra sp. using mice as test animals White mice are artificially infested nasally, buccally, or ocularly with 5 newly-hatched larvae of *Cuterebra sp.* For dermal tests, 48 hours later a plastic collar is placed around the neck of each male mouse, and the portion of the body behind the collar is dipped in 200 ml of an emulsion of candidate compound. A standard emulsifiable concentrate consists of 25 parts candidate compound, 65 parts of xylene and 10 parts octylphenoxy polyethoxy ethanol of average molecular weight equal to 628 and having from 9 to 10 ethylene oxide units.

At 4 days posttreatment, the skin of each mouse is examined carefully for encapsulated, live larvae. Effectiveness of the treatments is determined by comparing numbers of larvae encapsulated in treated mice with numbers in untreated mice. Usually 3 mice/concentration are treated. If mice or the larvae are killed at the initial concentration of 1%, lower concentrations (0.6, 0.3, 0.2, 0.1%, etc.) are tested until there is no systemic activity or the mice survive.

For the oral tests, 48 hours after infestation, female mice are treated orally by use of a stomach tube consisting of a ½ inch length of polyethylene tubing (ID, 0.034 in.; OD, 0.050 in.) fitted over the end of a 20-gauge needle attached to a 0.25-cc syringe. Mice are individually weighed and dosed with the appropriate amount of candidate compound formulated in polyoxyethylene (20) sorbitan monolaurate.

At 4 days posttreatment, the skin of each mouse is examined carefully for encapsulated, live larvae. Effectiveness of the treatments is determined by comparing numbers of larvae encapsulated in treated mice with numbers in untreated mice. Usually 3 mice/dosage are treated. If the mice or the larvae are killed at the initial dosage of 100 mg/kg, lower dosages (60, 30, 20, 10 mg/kg, etc.) are administered until there is no systemic activity or mice survive.

Mortality data are subjected to log-probit analysis in order to determine dosages or concentrations that kill 50 or 90% of the larvae.

The data obtained are recorded in Table I below.

TABLE I

Evaluation of the Efficacy of compounds of the invention for the control of *Cuterebra* sp. using mice as test animals.

| Treatment | Oral (mice) Dosage (mg/kg) | | Dermal (mice) Dosage (%) | |
|---|---|---|---|---|
| | LD$_{50}$ | LD$_{90}$ | LC$_{50}$ | LC$_{90}$ |
| Cl—⟨phenyl⟩(—NH—C(=S)—NH—P(=O)(OC$_2$H$_5$)$_2$)(—NH—C(=S)—NH—P(=O)(OC$_2$H$_5$)$_2$) | 4.86 | 8.22 | 0.031 | 0.086 |
| Cl—⟨phenyl⟩ with NH—C(=S)—NH—P(=O)(OC$_2$H$_5$)$_2$ at two positions | 58.01 | 151.84 | 0.18 | 0.43 |
| ⟨phenyl⟩(—NH—C(=S)—NH—P(=O)(OC$_2$H$_5$)$_2$)(—NH—C(=S)—NH—P(=O)(OC$_2$H$_5$)$_2$) | 14.1 | 24.3 | 0.06 | 0.15 |

We claim:

1. A method for the control of larvae of flies of the family Hypodermatidae infesting ruminants and other warm-blooded animals comprising administering to said infested host animal a larvicidally effective amount of a compound having the formula:

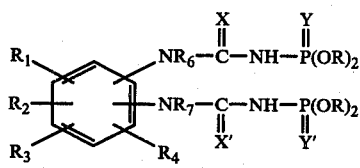

wherein R is alkyl ($C_1$–$C_4$); $R_1$ represents a member selected from the group consisting of hydrogen, alkyl ($C_1$–$C_4$), fluoro, chloro, bromo, iodo, $R_5O$, $R_5S(O)_n$ and $CF_3$; $R_2$, $R_3$ and $R_4$ each represent hydrogen, methyl and halo; $R_5$ represents a member selected from the group consisting of alkyl ($C_1$–$C_4$), benzyl and phenyl; $n$ represents an integer from 0 to 2; and X, X', Y and Y' each represent members selected from the group consisting of oxygen or sulfur, provided that X, X', Y and Y' cannot all be O or all be S, and X and X' cannot both be O when Y and Y' are both S.

2. The method according to claim 1, wherein said compound is characterized by the formula:

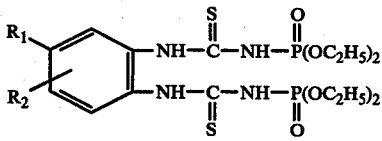

wherein $R_1$ is a member selected from the group consisting of n-butyl, methoxy, benzyloxy, phenoxy, n-butylthio, benzylthio, phenylthio, phenylsulfinyl, phenylsulfonyl, fluoro, chloro, bromo, iodo and $CF_3$; $R_2$ represents hydrogen, methyl or chloro.

3. The method according to claim 1, wherein said compound is characterized by the formula:

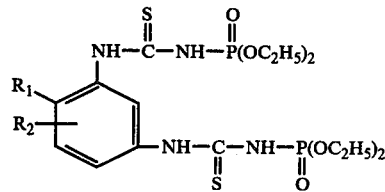

wherein $R_1$ represents methoxy or chloro; and $R_2$ represents hydrogen or methyl.

4. The method according to claim 1, wherein said compound is characterized by the formula:

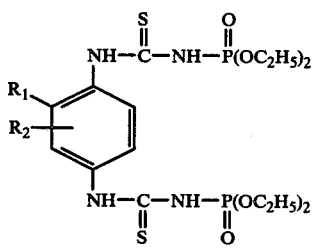

wherein $R_1$ is a member selected from the group consisting of methoxy, phenoxy, methylthio, n-propylthio, benzylthio, phenylthio, fluoro, chloro, bromo, iodo and $CF_3$; $R_2$ represents hydrogen, methyl or chloro.

5. The method according to claim 1, wherein said compound is {(4-chloro-o-phenylene)bis[imino(thiocarbonyl)]}-diphosphoramidic acid, tetraethyl ester.

6. The method according to claim 1, wherein said compound is {(2-chloro-p-phenylene)bis[imino(thiocarbonyl)]}-diphosphoramidic acid, tetraethyl ester.

7. The method according to claim 1, wherein said animals are cattle, and the compound is administered to the host animal in the form of a single oral dose at a dosage level of from 0.5 to 100 mg/kg of animal body weight.

8. The method according to claim 1, wherein said animals are cattle and the compound is administered in animal feed containing from 0.006% to 0.2% by weight of said compound.

9. The method according to claim 1, wherein said animals are cattle and the compound is administered from a liquid solution to said animals skin in amounts of from 0.5 to 100 mg/kg animal body weight.

10. The method according to claim 1, wherein said animals are cattle and the compound is administered parenterally to said animals in amounts of from 0.5 to 100 mg/kg animal body weight.